(12) United States Patent
Moore

(10) Patent No.: US 9,066,731 B2
(45) Date of Patent: Jun. 30, 2015

(54) INSTRUMENT FOR REMOVING TISSUE

(75) Inventor: Gary Moore, Leeds (GB)

(73) Assignee: DEPUY INTERNATIONAL LIMITED (GB)

( * ) Notice: Subject to any disclaimer, the term of this patent is extended or adjusted under 35 U.S.C. 154(b) by 827 days.

(21) Appl. No.: 12/809,823

(22) PCT Filed: Dec. 12, 2008

(86) PCT No.: PCT/GB2008/004089
§ 371 (c)(1),
(2), (4) Date: Jun. 21, 2010

(87) PCT Pub. No.: WO2009/081095
PCT Pub. Date: Jul. 2, 2009

(65) Prior Publication Data
US 2010/0280518 A1    Nov. 4, 2010

(30) Foreign Application Priority Data

Dec. 21, 2007   (GB) .................................. 0725024.4

(51) Int. Cl.
*A61B 17/32*   (2006.01)
*A61B 17/16*   (2006.01)

(52) U.S. Cl.
CPC ......... *A61B 17/1666* (2013.01); *A61B 17/1617* (2013.01); *A61B 17/1624* (2013.01)

(58) Field of Classification Search
USPC ........ 606/79–81, 91, 171, 180; 433/144, 165, 433/166
See application file for complete search history.

(56) References Cited

U.S. PATENT DOCUMENTS

| | | | |
|---|---|---|---|
| 2,910,978 A | | 3/1955 | Urist |
| 3,630,204 A | * | 12/1971 | Fishbein .......................... 606/81 |
| 6,347,941 B1 | * | 2/2002 | Boston ........................... 433/165 |
| 2004/0073224 A1 | | 4/2004 | Bauer |
| 2006/0195110 A1 | * | 8/2006 | White et al. ..................... 606/81 |

FOREIGN PATENT DOCUMENTS

| | | | | |
|---|---|---|---|---|
| DE | 198709738 U1 | | 11/1987 | |
| DE | G 87 09 738.9 | * | 11/1987 | ................ A61F 2/34 |
| DE | 101 48 022 A1 | * | 5/2003 | ................ A61F 2/46 |
| DE | 10148022 A1 | | 5/2003 | |
| EP | 328478 A1 | | 8/1989 | |
| WO | WO 03086208 A1 | | 10/2003 | |
| WO | WO 2008081307 A2 | | 7/2008 | |

OTHER PUBLICATIONS

PCT Search Report and Written Opinion PCT/GB2008/004089 dated Aug. 18, 2009.
UK Search Report GB0725024.4—search date Mar. 19, 2008.

* cited by examiner

*Primary Examiner* — Anu Ramana
*Assistant Examiner* — Jessica Weiss

(57) ABSTRACT

An instrument for removing tissue from a bone to create a cavity consists of an approximately spherical body having cutting formations in its external surface for cutting a bone. The body has a connector by which it can be connected to a drive by which it can be rotated about an axis, and a recess at the pole, opposite the connector. When the instrument is applied to the surface of a bone and is rotated about its axis, bone is cut as a result of the action of the formations against the bone, and a circular region of bone adjacent to the polar recess in the body remains generally intact.

17 Claims, 3 Drawing Sheets

INSTRUMENT FOR REMOVING TISSUE

CROSS REFERENCE TO RELATED APPLICATION

This application is a National Stage 35 U.S.C. 371 of International Patent Application PCT/GB2008/004089 filed Dec. 12, 2008.

BACKGROUND OF THE INVENTION

This invention relates to an instrument for removing tissue from a bone to create a cavity.

The acetabular component of common hip joint prostheses comprises a part-spherical shell which can be implanted in the patient's acetabulum. Generally the shell is formed from a metallic material. A liner component is fitted to the shell. The liner component is formed from a polymeric material such as an ultrahigh molecular weight polyethylene (UHMWPE) and provides the bearing surface for articulation with the convex head of a femoral component.

U.S. Pat. No. 2,910,978 discloses an acetabular component which has a notch formed in it. The notch has a rounded portion towards the pole of the component, and a narrower neck portion which extends from the rounded portion to the peripheral edge of the component. The notch allows fat pad tissue in the acetabular fossa to be preserved when the acetabulum is prepared to receive the prosthesis component. This can promote lubrication of the joint during articulation.

BRIEF SUMMARY OF THE INVENTION

The present invention provides an instrument for removing tissue from a bone to create a cavity, which comprises an approximately spherical body having cutting formations in its external surface for cutting a bone, the body having a connector by which it can be connected to a drive by which it can be rotated about an axis, the body having a recess in it at the pole, opposite the connector, so that, when the instrument is applied to the surface of a bone and is rotated about its axis, bone is cut as a result of the action of the formations against the bone, and a circular region of bone adjacent to the polar recess in the body remains generally intact.

The instrument of the invention can enable a recess to be cut in a bone, leaving tissue adjacent to a polar region of the instrument intact. The intact tissue can then be located within the notch of an acetabular component of a hip joint prosthesis. By careful selection of the tissue which is left intact, this arrangement can provide an advantage of improved lubrication of the joint during articulation after implantation.

Preferably, the cutting formations are provided on the surface of the body over an area which extends from the recess beyond the equator of the body, and in which the angle subtended at the centre of the body between the polar axis and a radius which connects the centre of the body and the cutting formation which is furthest from the polar recess is at least about 100°. This can enable a cavity to be formed in a bone which has a shape which forms part of a sphere, in which the angle subtended by spherical surface of the bone measured from the polar axis can exceed 90°. This can help to minimise the amount of healthy bone is removed using the instrument.

Preferably, the recess at the pole of the body is approximately circular. This can be consistent with creating a cavity in which a tissue in a circular region at the pole of the body remains intact. Preferably, the angle subtended by the recess at the centre of the body is at least about 30°, more preferably at least about 40°. Preferably, the angle subtended by the recess at the centre of the body is not more than about 65°, more preferably not more than about 55°.

Preferably, the angle subtended at the centre of the body between the polar axis and a radius which connects the centre of the body and the cutting formation which is furthest from the polar recess is at least about 120°, more preferably at least about 130°, for example at least about 140°. Preferably, the angle subtended at the centre of the body between the polar axis and a radius which connects the centre of the body and the cutting formation which is furthest from the polar recess is not more than about 170°, more preferably at least about 160°, for example at least about 150°.

Preferably, the cutting formations are distributed over the surface of the body between the recess at the pole of the body and a region surrounding the connector. The region which surrounds the connector will generally be approximately circular.

Preferably, the instrument includes a connector shaft by which the body can be connected to a drive unit, the connector shaft being capable of being connected to the connector on the body, and having non-aligned first and second shaft parts which are arranged so that rotational drive can be transmitted from a drive unit to the body through a non-zero angle.

Preferably, the body has at least one cutting formation within the polar recess. A cutting formation within the recess can comprise an opening which extends through the body, defined by one or more raised lips, each having a cutting edge (in the manner of the cutting formations on a grating device such as might be used in food preparation). The cutting formation can be in the form of a slit. The slit can be straight. The slit can be curved.

It can be preferred for a cutting formation within the recess to be in the form of a sharp ridge extending along the wall of the recess. The use of such ridges to cut tissue is known in surgical instruments, for example in relation to burr instruments. Preferably, a plurality of sharp ridges are provided on the wall of the recess. The use of ridges for the cutting formations in the recess can have the advantage that the risk of damaging soft tissue located close to bone tissue is reduced. Factors affecting the design of the cutting formations, including for example the number of formations, their size and shape, and their arrangement on the surface of the instrument, can be selected based on knowledge of existing surgical instruments.

Preferably, the body has an array of cutting formations in the wall which defines the polar recess. The cutting formations are preferably spaced apart approximately uniformly around the recess.

The recess in the body can be a blind recess so that, in the region of the recess, the body has an external surface but the surface is recessed relative to the surface in the adjacent regions of the body. Preferably the depth of the recess is at least about 3 mm, more preferably at least about 5 mm. Preferably the depth of the recess is not more than about 10 mm, more preferably not more than about 7 mm. Especially when the body is hollow, the recess can be open so that it communicates directly with the interior of the body.

The cutting formations in the external surface of the spherical body can comprise a plurality of sharp ridges extending generally between the pole and the peripheral edge of the body. When the body is hollow, the cutting formations can comprise a plurality of openings which extend through the body, each defined by one or more raised lips, each having a cutting edge (in the manner of the cutting formations on a grating device such as might be used in food preparation). If desired, such a body can be arranged to cut tissue when the head is rotated in both rotational directions by having the cutting edges of the raised lips facing in two opposite directions. Such oppositely facing cutting edges can be provided on a common opening in the body. First and second sets of openings can be provided, in which the cutting edges on the openings of the first set face in a direction which is opposite to that of the cutting edges on the openings of the second set.

Preferably, the body has discharge formations in its external surface which facilitate discharge of cut bone debris from the space between the external surface of the body and the surface of the bone. For example, the discharge formations can comprise grooves formed in the external surface of the body. When the body is hollow, the discharge formations can comprise openings which extend through the body.

Cutting formations and discharge formations which can be incorporated in the body of the instrument of the invention are known from existing bone cutting devices, especially for preparing a cavity in the acetabulum and also for preparing bone in other surgical procedures.

The overall shape of the body will usually be approximately part-spherical. However, it might be that the shape will deviate from spherical, for example by varying the radius of the head slightly between the pole of the head and its equatorial region. The size of the body will be selected according to the desired size of the cavity in the acetabulum and therefore the size of the component of the hip joint prosthesis which is to be implanted in the prepared cavity. The radius of the body will usually be at least about 15 mm, for example at least about 20 mm. The external radius of the body will usually be not more than about 50 mm. Examples of sizes of the body include 28 mm and 42 mm.

The connector by which the body can be fastened to a drive unit can be provided on a bar which extends across the body on the face which is opposite to the bone engaging surface thereof. The bar can be provided at the peripheral edge of the body, which can be particularly preferred when the head has a reinforced rim. The bar can however be recessed within the head. The bar can engage the rotation drive unit using features such as hooks, retractable pins, bayonet type formations and the like. Suitable features for fastening the body of a bone-cutting reamer device to a drive unit are known from existing surgical instruments.

The body can be made from materials which are commonly used in the manufacture of surgical instruments. It will often be preferred to make the body from a selected stainless steel which is suitably biocompatible, which can withstand the forces imposed on it when in use, and which lends itself to manufacture using conventional processing techniques.

The shape of the recess in the body will be chosen having regard to the shape of the tissue within the cavity in the bone which is to be left relatively undisturbed.

In another aspect, the invention provides a method of forming a cavity in a bone using an instrument of the kind which is discussed above, which comprises:
  a. causing the body to rotate about its polar axis,
  b. moving the body against the bone along an introducing axis, in which the angle between the polar axis and the introducing axis is at least about 5°.

The method of the invention has the advantage that the body part of the instrument of the invention can be inserted into the body cavity along the same axis as the axis on which the prosthesis component is subsequently implanted. In this way, the risk of tissue that is left intact in the reaming step interfering with implantation of the prosthesis component is reduced, compared with techniques in which the reaming step takes place on an axis which is different from the axis on which the prosthesis component is implanted.

Furthermore, by using a body in which the angle subtended at the centre of the body between the polar axis and a radius which connects the cutting formation which is furthest from the polar recess and the centre of the body is at least about 120°, a cavity can be formed in a bone which has a shape which forms part of a sphere, in which the angle subtended by spherical surface of the bone measured from the polar axis can exceed 90°. This can help to minimise the amount of healthy bone is removed using the instrument, in particular compared with a technique in which a cutting body is inserted along the axis about which it is rotated.

BRIEF DESCRIPTION OF THE DRAWINGS

Embodiments of the invention will now be described by way of example with reference to the accompanying drawings, in which.

DETAILED DESCRIPTION OF THE INVENTION

Figure 1:
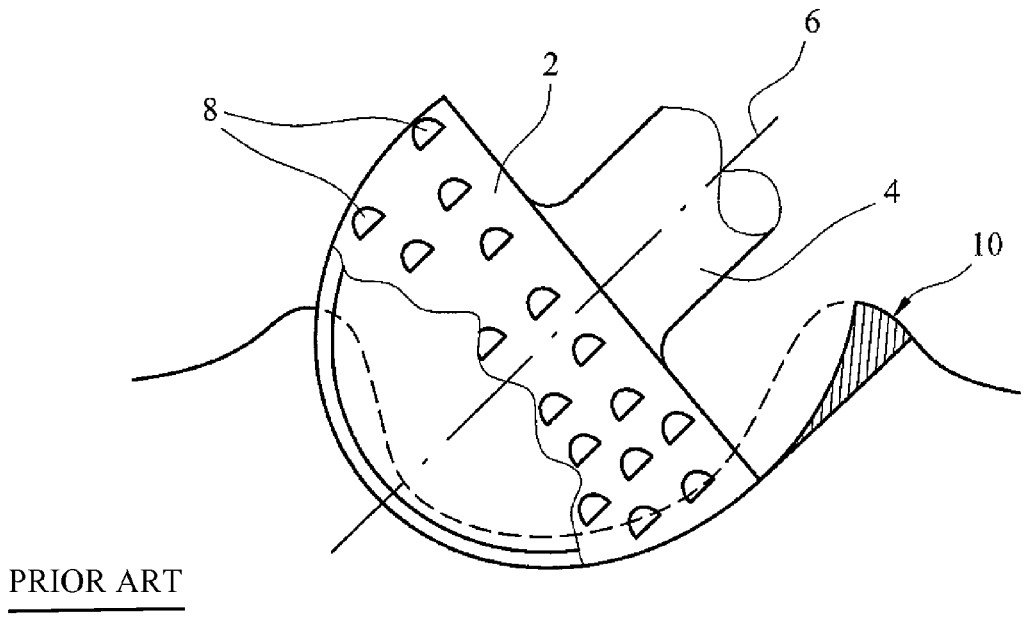
FIG. 1 is a view along the anterior posterior axis, partially in section, through an acetabulum during a reaming step using a conventional reaming instrument.

Referring to the drawings, FIG. 1 is a view of a patient's acetabulum along the anterior-posterior axis. It shows a reamer instrument which comprises a reamer head 2, provided on a shaft 4. A rotary drive can be imparted to the reamer head through the shaft which defines the axis of rotation 6 of the head. As is known, the drive can be imparted using a powered drive unit (not shown). The head can be fastened detachably to the shaft, for example using a bayonet arrangement, as is known.

The reamer head comprises a hollow shell which is approximately hemispherical. It is formed form a sheet of stainless steel. It has a plurality of openings 8 which extend through the shell defined by one or more raised lips, each having a cutting edge (in the manner of the cutting formations on a grating device such as might be used in food preparation). The openings are spaced apart over the surface of the shell (the structure shown in FIG. 1 shows only part of the surface of the shell). When the reamer head is rotated while in contact with bone tissue, the cutting teeth cause the bone to be cut.

A conventional acetabular reamer instrument as shown in FIG. 1 is typically moved against the acetabulum along the axis 6 about which the reamer head is rotated. This can cause the acetabular cavity to be shaped so that it has an approximately part spherical shape, with the pole of the sphere on the axis about which the head is rotated.

The movement of the reamer head against the bone along the axis about which it is rotated means that the spherical surface of the prepared cavity cannot extend beyond an angle of 90° relative to the polar axis. This can mean that healthy bone tissue at the lateral edge 10 of the acetabulum can be removed unnecessarily.

Figure 2:
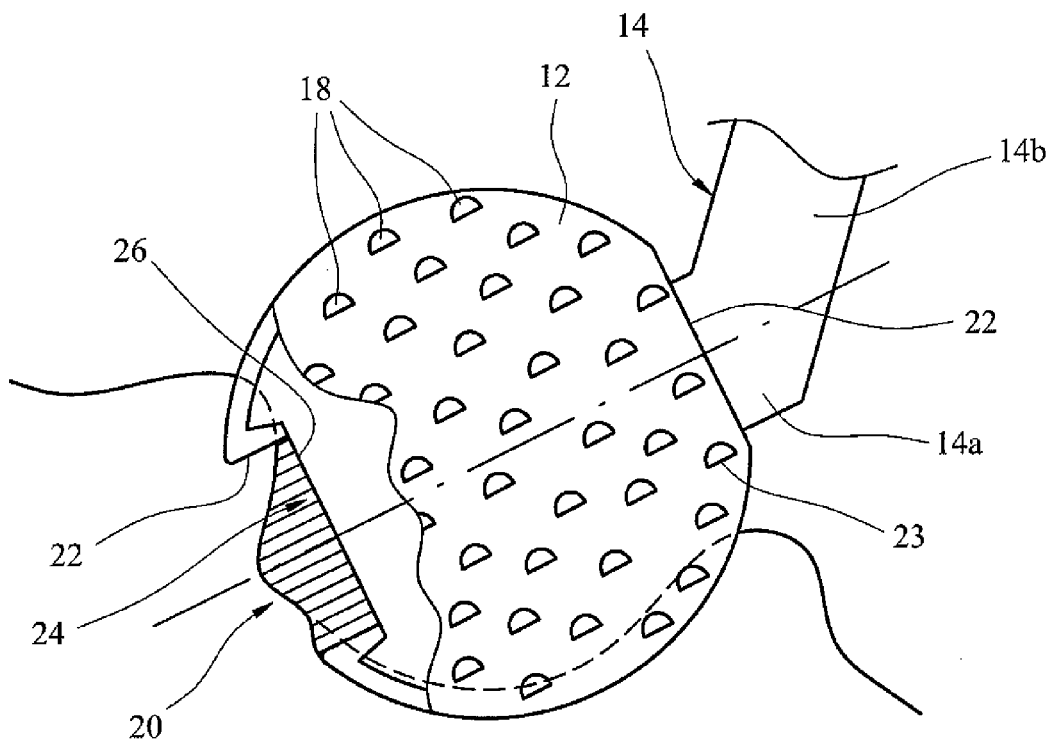
FIG. 2 is a view along the anterior posterior axis, partially in section, through an acetabulum during a reaming step using a reaming instrument according to the present invention.
Figure 3:
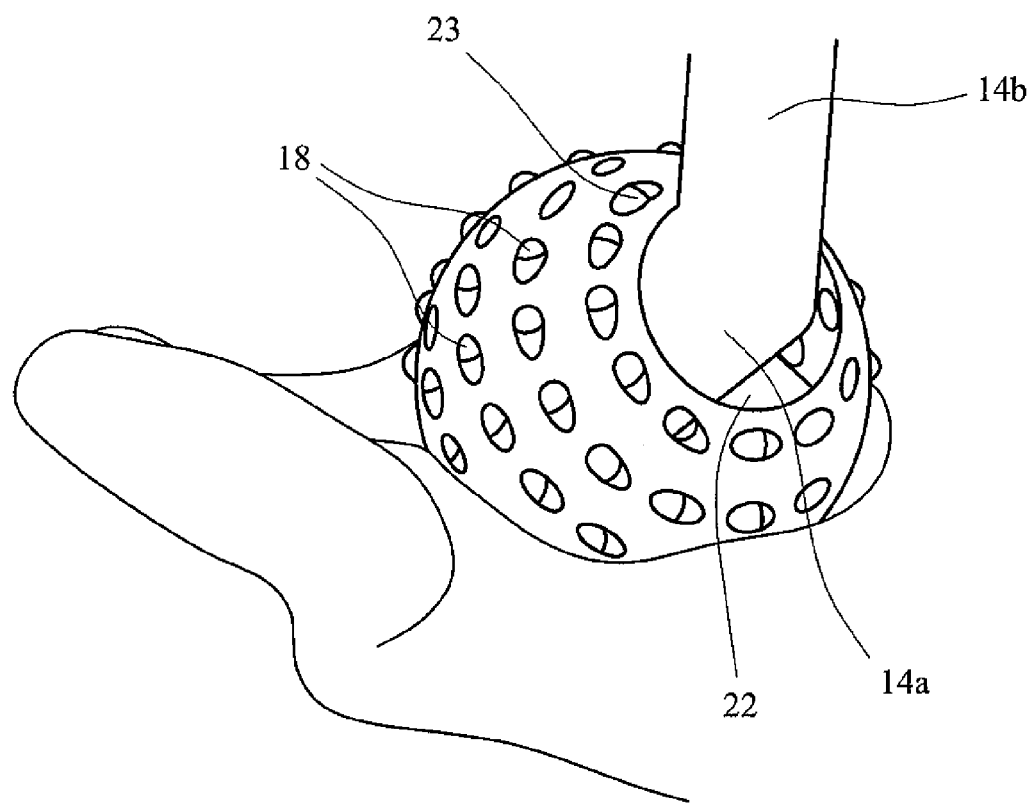
FIG. 3 is an isometric view generally along the posterior-anterior axis of the reaming instrument of the present invention.

FIGS. 2 and 3 show an instrument according to the invention which comprises a reamer head 12, provided on a cranked shaft 14 having a first crank arm 14*a* to which the reamer head is connected and a second crank arm 14*b* which extends from the acetabular cavity to a drive unit. The angle between the first and second crank arms is about 30°. A rotary drive can be imparted to the reamer head through the first and second crank arms 14*a*, 14*b* to cause the reamer head to rotate about the axis which is defined by the first crank arm 14*a*. The drive can be imparted using a powered drive unit (not shown). The head can be fastened detachably to the first crank arm, for example using a bayonet arrangement, as is known.

The reamer head comprises a hollow shell which is shaped as part of a sphere. A recess in the form of a polar opening 20 is provided at the pole of the shell. A connector opening 22 is provided at the opposite end of the polar axis, at which the shell is connected to the shaft. Accordingly, the cutting formations are provided on the surface of the shell over an area which extends from the polar opening beyond the equator of the shell, so that the angle a$\alpha$ subtended at the centre of the shell between the polar axis and a radius which connects the cutting formation 23 which is furthest from the polar recess and the centre of the body is more than about 100°, preferably not more than about 150°, for example about 130°.

The reamer head is formed from a sheet of stainless steel. It has a plurality of openings 18 arranged over its surface between the polar opening and the connector opening extending through the shell, defined by one or more raised lips, each having a cutting edge (in the manner of the cutting formations on a grating device such as might be used in food preparation). When the reamer head is rotated while in contact with bone tissue, the cutting teeth cause the bone to be cut.

While the reamer head shown in FIG. 2 has cutting formations in the form of openings which extend through the hollow shell, it can be preferred for some applications for the cutting formations on a cutting head (which need not be hollow) to be provided in the form of a sharp ridges extending along the external surface of the head.

The polar opening 20 is circular when viewed along the axis of the head, has an axially extending annular wall 22 which is arranged so that it extends approximately parallel to the polar axis. The annular wall has a plurality of sharp ridges arranged on it.

In use, the cutting head can be applied to bone tissue in a direction which is generally parallel to the second crank arm 14*b*, while the reamer head 12 is rotated about an axis which is aligned with the first crank arm 14*a*. Tissue which is in contact with the surface of the reamer head is cut by it. The provision of cutting formations on the surface of the shell over an area which extends from the polar opening beyond the equator of the shell means that healthy bone tissue at the lateral edge 10 of the acetabulum need not be removed unnecessarily.

Tissue 24 which is located adjacent to the pole of the reamer head 12 within the polar opening 20 is not cut by the reamer head. Accordingly, this tissue remains intact, as a plug of tissue extending through the polar opening into the space within the hollow reamer head. The ridges on the annular wall 22 of the polar opening cause tissue 26 which faces the annular wall along the direction in which the reamer head is advanced to be cut.

Figure 4:
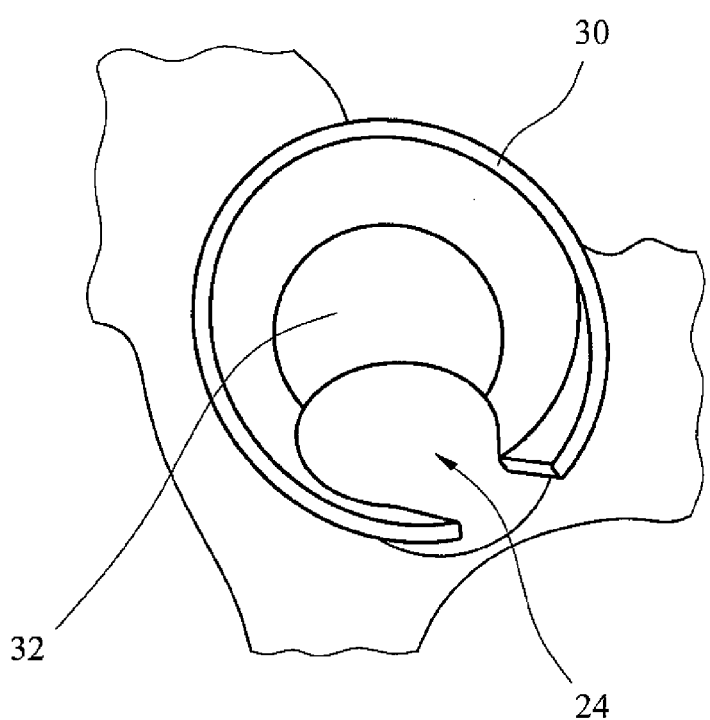
FIG. 4 is a view along the medial lateral axis showing an acetabulum with the acetabular component of a hip joint prosthesis implanted within it.

FIG. 4 shows an acetabular component 30 of a hip joint prosthesis positioned in a prepared acetabulum. The acetabular component comprises a hollow shell with a circular notch 32 formed in it. The acetabular component 30 is positioned in the acetabulum by moving it along an axis which is parallel to the axis along which the reamer head 12 was moved in the reaming step. The component can be positioned in the acetabulum so that the tissue 24 which remains intact as a plug after the reaming step extends through the notch. This is facilitated by the shape of the plug which results from moving the reamer head along an axis which is non-parallel to the axis about which the head is rotated. The plug of tissue can help to provide lubrication to the joint during articulation.

Figure 5:
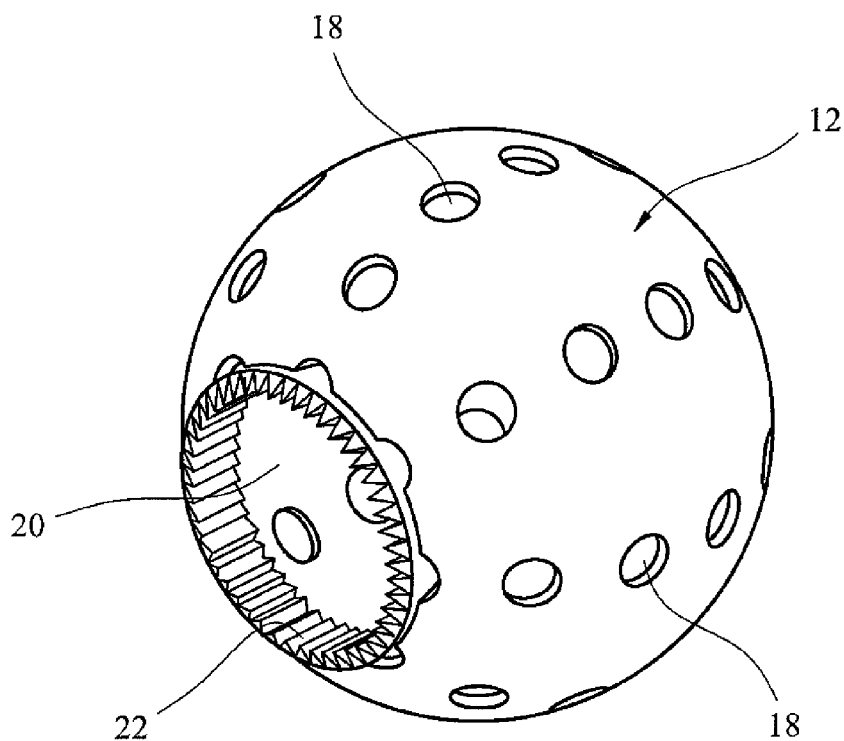
FIG. 5 is an isometric view of the reamer head of the instrument which is shown in FIG. 2.
Figure 6:
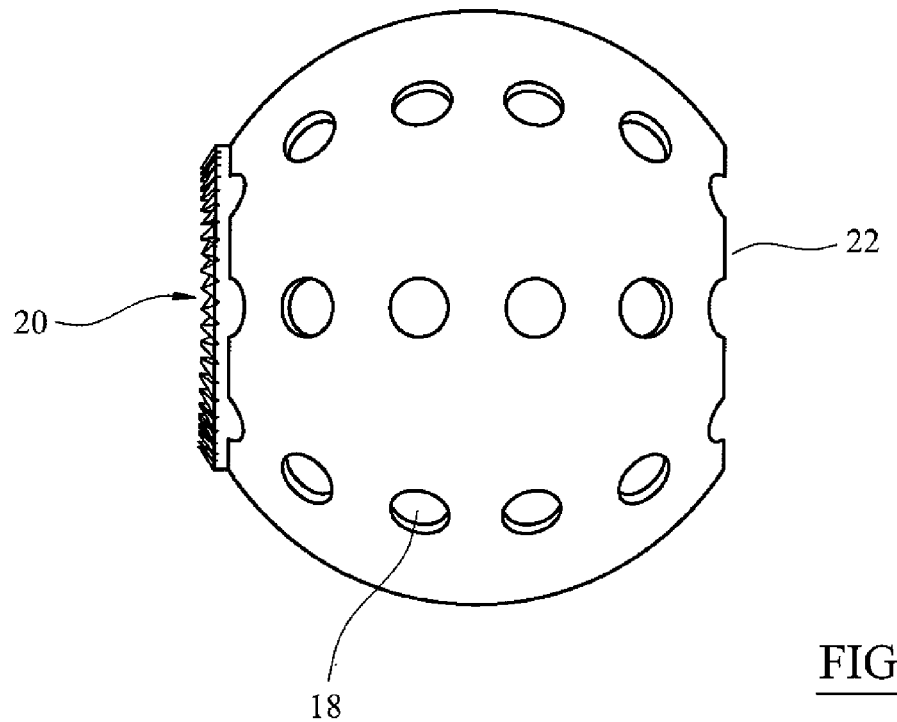
FIG. 6 is a side view of the reamer head shown in FIG. 5.

FIGS. 5 and 6 show the reamer head component of the instrument. The same reference numerals are used in FIGS. 5 and 6 as in earlier Figures discussed above.

The invention claimed is:

1. An instrument for removing tissue from a bone to create a cavity, comprising:
   a spherical body having a pole, an equator, a center, a polar axis, an inner surface, an external surface, a polar edge defined as a line, near the pole, where the external surface and the inner surface meet, and cutting formations formed in the external surface for cutting the bone, the body being rotatable about the polar axis, the body having a polar recess formed at the pole, the polar recess being defined at least in part by the polar edge, and a plurality of cutting ridges extending from the inner surface adjacent the polar edge toward the polar axis; and
   wherein the angle subtended at the center of the body between (a) the polar axis and (b) a radius that connects a cutting formation that is furthest from the polar recess and the center of the body, is at least 100°.

2. The instrument of claim 1, wherein the polar recess of the body is circular when the body is viewed along the polar axis.

3. The instrument of claim 2, wherein the angle subtended at the center of the body by the polar recess is at least 140°.

4. The instrument of claim 2, wherein the angle subtended at the center of the body by the polar recess is not more than 170°.

5. The instrument of claim 1, further comprising:
   a connector attached to the body at a location spaced from the pole;
   a connector shaft detachably connected at one end to the connector and at the other end to a drive, the connector shaft comprising a first shaft portion and a second shaft portion, the first shaft portion connected to the second shaft portion at an angle such that the first shaft portion and the second shaft portion are not aligned.

6. The instrument of claim 1, wherein the plurality of cutting ridges are spaced uniformly around the polar recess.

7. The instrument of claim 1, wherein the depth of the polar recess is at least 2 mm.

8. A method of forming a cavity in a bone using the instrument of claim 1, comprising the steps of:
   causing the body to rotate about the polar axis;
   moving the body against the bone along an introducing axis, wherein the angle between the polar axis and the introducing axis is at least 5°.

9. The instrument of claim 1, wherein the polar recess is formed about the polar axis.

10. The instrument of claim 1, wherein the cutting formations are provided on the external surface over an area that extends from the polar recess to a point beyond the equator of the body.

11. The instrument of claim 1, wherein the polar recess has a larger area than the area of any one of the cutting formations.

12. The instrument of claim 1, wherein the body has a proximal and a distal end, and the inner surface of the body comprises an annular wall that defines the polar recess, the annular wall extending from the distal end toward the proximal end in a plane parallel to the polar axis.

13. The instrument of claim 12, wherein the plurality of cutting ridges are formed on the surface of the annular wall.

14. An instrument for removing tissue from a bone to create a cavity, comprising:
   a spherical body having a pole, an equator, a center, a polar axis, an inner surface, an external surface, a polar edge defined as a line, near the pole, where the external surface and the inner surface meet, and cutting formations formed in the external surface for cutting the bone, the body being rotatable about the polar axis, the body having a polar recess formed at the pole, the polar recess being defined at least in part by the polar edge, and a plurality of cutting ridges extending from the inner surface adjacent the polar edge toward the polar axis; and
   wherein the cutting formations are provided on the external surface over an area that extends from the polar recess to a point beyond the equator of the body.

15. The instrument of claim 14, wherein the polar recess of the body is circular when the body is viewed along the polar axis.

16. The instrument of claim 14, wherein the body has at least one cutting formation within the polar recess.

17. The instrument of claim 14, wherein the depth of the polar recess is at least 2 mm.

* * * * *